(12) United States Patent
Bhatarah et al.

(10) Patent No.: US 8,530,679 B2
(45) Date of Patent: Sep. 10, 2013

(54) DELTA 9—TETRAHYDROCANNABINOL PROCESSING

(75) Inventors: Parveen Bhatarah, Stevenage (GB); Alan Kenneth Greenwood, Stevenage (GB); Derek McHattie, Stevenage (GB); Jerome Thomas Garfield Carr-Brion, Stevenage (GB)

(73) Assignee: Resolution Chemicals Limited, Stevenage, Herts (GB)

( * ) Notice: Subject to any disclaimer, the term of this patent is extended or adjusted under 35 U.S.C. 154(b) by 692 days.

(21) Appl. No.: 12/528,077

(22) PCT Filed: Feb. 19, 2008

(86) PCT No.: PCT/GB2008/000579
§ 371 (c)(1),
(2), (4) Date: Nov. 17, 2009

(87) PCT Pub. No.: WO2008/102129
PCT Pub. Date: Aug. 28, 2008

(65) Prior Publication Data
US 2010/0087518 A1    Apr. 8, 2010

(30) Foreign Application Priority Data
Feb. 20, 2007    (GB) .................................. 0703284.0

(51) Int. Cl.
*C07D 311/80* (2006.01)
*C07D 311/82* (2006.01)
*B01D 11/00* (2006.01)
*B01D 3/24* (2006.01)
*B01D 15/00* (2006.01)

(52) U.S. Cl.
USPC ........... 549/388; 549/390; 210/634; 210/636; 203/39; 203/41; 203/73; 203/74; 203/80; 203/91

(58) Field of Classification Search
USPC ........... 549/388, 390; 210/634, 636; 203/39, 203/41, 73, 74, 80, 91
See application file for complete search history.

(56) References Cited

U.S. PATENT DOCUMENTS

| | | | |
|---|---|---|---|
| 5,447,719 A * | 9/1995 | Kamataki | 424/741 |
| 5,804,592 A * | 9/1998 | Volicer | 514/454 |
| 6,365,416 B1 | 4/2002 | Elsohly et al. | |
| 6,403,126 B1 * | 6/2002 | Webster et al. | 424/776 |
| 2002/0031480 A1 | 3/2002 | Peart et al. | |
| 2003/0017216 A1 * | 1/2003 | Schmidt et al. | 424/725 |
| 2003/0050334 A1 * | 3/2003 | Murty et al. | 514/454 |

FOREIGN PATENT DOCUMENTS

| | | |
|---|---|---|
| GB | 2 408 978 A | 6/2005 |
| WO | 03/064407 A3 | 8/2003 |
| WO | 2004/026857 A3 | 4/2004 |
| WO | WO2004/043946 | 5/2004 |
| WO | 2006/053766 A1 | 5/2006 |
| WO | 2006/136273 A1 | 12/2006 |
| WO | WO2007/041167 | 4/2007 |

OTHER PUBLICATIONS

Nelson, Hemp Husbandry Cannabinoid Chem. Ch. 6 (2000).*
Cyranski, Michal, et al, to What Extent can Aromaticity be Defined Uniquely?, 67 J Org.Chem. 1333 (2002).

* cited by examiner

*Primary Examiner* — Andrew D Kosar
*Assistant Examiner* — Raymond Covington
(74) *Attorney, Agent, or Firm* — Knobbe, Martens, Olson & Bear, LLP

(57) ABSTRACT

The present invention provides a process for handling Δ9-THC, which comprises preparing a solution of Δ9-THC in a solvent which exists as a gas at room temperature and atmospheric pressure. The invention also provides solutions of Δ9-THC in the solvent and solid preparations of Δ9-THC.

17 Claims, No Drawings

DELTA 9—TETRAHYDROCANNABINOL PROCESSING

This application is U.S. National Phase of International Application PCT/GB2008/000579, filed Feb. 19, 2008 designating the U.S., and published in English as WO 2008/102129 on Aug. 28, 2008, which claims priority to Great Britain Patent Application No. 0703284.0, filed Feb. 20, 2007.

The present invention relates to processes for the handling of Δ9-tetrahydrocannabinol (Δ9-THC) that are useful in its manufacture and storage.

Cannabinoids are a family of naturally occurring $C_{21}$ terpenophenolic compounds uniquely produced in cannabis. Marijuana usually refers to a mixture of leaves and flowering heads of the pistillate plant of *Cannabis sativa* from which tetrahydrocannabinols (THCs) are isolated. THCs contain two main isomeric forms, depending on the position of the double bond. The position of the double bond and the stereochemistry of these THCs have been confirmed by nuclear magnetic resonance and X-ray structure.

THCs have been used as psychomimetic agents for many years with the main psychomimetic activity being attributed to Δ9-THC (20 times greater than Δ8-THC). Δ9-THC is marketed as Marinol™ and is prescribed for patients suffering from severe nausea and vomiting associated with cancer chemotherapy.

The major cannabinoids present in cannabis other than Δ9-THC and Δ8-THC are cannabinol, cannabidiol and Δ9-THC carboxylic acid which exists in two forms depending on the position of the carboxylate group. Cannabidiol may be present in cannabis in large amounts but has little activity.

The major component of cannabis is Δ9-THC carboxylic acid which exists as two isomeric forms, THCA-A and THCA-B, both of which are psychomimetically inactive. It can be converted into the predominately active constituent Δ9-THC, slowly on storage and rapidly on exposure to heat (e.g. when smoked). In fresh, dried marijuana, 95% of cannabinoids are present as THCA-A. Only THCA-A can be readily decarboxylated to Δ9-THC due to the presence of hydrogen bonding.

It is known to extract active ingredients from cannabis plant material using ethanol or a mixture of ethanol and water. The extract typically contains large amounts of Δ9-THC and Δ9-THC carboxylic acid and the acid is converted to Δ9-THC by refluxing the cannabis extract in ethanol. Δ9-THC is then purified.

Δ9-THC is a glassy solid material that is difficult to handle during manufacture as it tends to stick to the walls of vessels making transfer to storage containers problematic.

Additionally, Δ9-THC is a relatively unstable molecule that is susceptible to rearrangement and oxidation at room temperature and is therefore usually stored in a dark container at low temperature. Even when handled under controlled conditions, decomposition of the Δ9-THC takes place limiting the length of time the product can be stored and the processing techniques that can be used.

It is therefore the object of the present invention to provide an alternative method and composition for the handling and storage of Δ9-THC.

Accordingly, the present invention provides for a process for handling Δ9-THC, which comprises preparing a solution of Δ9-THC in a solvent which exists as a gas at room temperature and atmospheric pressure.

In some embodiments the solvent can be an organic solvent having a boiling point below room temperature. Thus, the Δ9-THC solution can be conveniently handled at atmospheric pressure and at a temperature below the boiling point of the solvent.

In alternative embodiments, the solvent can be an inorganic compound which exists as a gas at room temperature and atmospheric pressure, but which can be maintained as a liquid under conditions of altered temperature and/or pressure conveniently obtainable in laboratory or commercial preparative environments. Suitably, supercritical carbon dioxide may be used as a solvent in the processes of the invention. It will be appreciated that carbon dioxide exists in a supercritical fluid state when maintained above its critical temperature (31.1° C.) and pressure (73 atm; $7.4 \times 10^6$ Pa) and under such conditions it is known as supercritical carbon dioxide. Use of supercritical carbon dioxide is particularly preferred in situations in which low toxicity and/or low environmental impact are important.

It will be understood that references to room temperature refer to a temperature of about 18 to about 23° C., typically about 20-23.5° C., for example 20° C.

The solvents used according to the invention can be a single compound or a mixture of compounds, each compound being a low boiling point solvent e.g. as described herein. Preferably the solvent will possess one or more of the following properties: low toxicity; low environmental impact; and prior approval for pharmaceutical use. For example, in some embodiments a hydrofluoroalkane (HFA) solvent is used. HFAs are widely used in inhalers and have been recognised as having no toxicity issues.

In embodiments of the invention in which an organic solvent is used, the solvent will typically have a boiling point below about 20° C., preferably below about 0° C. The solvent conveniently has a boiling point of from about −60° C. to about 20° C., preferably from about −60° C. to about 0° C. Preferred boiling point ranges include about −60 to about −40° C., about −40 to about −20° C. and about −20 to about 0° C. Such solvents may be referred to herein as "low boiling point solvents".

The organic solvent of the invention may be any suitable low boiling point solvent, or a mixture of such solvents, having one or more of the properties described herein. In some embodiments, the solvent is a hydrocarbon solvent but other, non-hydrocarbon, organic solvents may also be used, for example low boiling point ethers.

In embodiments in which a hydrocarbon solvent is used, the hydrocarbon solvent typically comprises one or more $(C_1-C_5)$ hydrocarbons, optionally substituted by halogen (e.g. a hydrofluoroalkane). The hydrocarbon can be saturated or unsaturated and, if unsaturated, typically comprises one or two unsaturated bonds. In preferred embodiments, the hydrocarbon solvent comprises one or more $(C_1-C_4)$ hydrocarbons, one or more $(C_3-C_5)$ hydrocarbons, and/or one or more $(C_1-C_2)$ hydrocarbons substituted by one or more halogens, preferably fluoro or chloro.

In a preferred embodiment, the hydrocarbon solvent comprises one or more propanes, butanes or butenes.

More preferably, the hydrocarbon solvent comprises one or more of n-propane, isopropane, cyclopropane, n-butane, isobutane and isobutylene.

Most preferably, the hydrocarbon solvent comprises n-propane, n-butane, isobutane or isobutylene.

The processes of the invention have successfully been carried out using isobutylene, propane, butane and cyclopropane.

By way of further example, the solvent can comprise any of the following compounds or mixtures thereof:

a. Chloromethane (Methyl chloride), $CH_3Cl$, b.p. $-24.2°$ C.
b. 1,1-Difluoroethane, $CHF_2$—$CH_3$, b.p. $-25°$ C.
c. Chloroethane (Ethyl chloride), $CH_3$—$CH_2Cl$, b.p. $12.3°$ C.
d. 1,1,1,2-Tetrafluoroethane (R-134a, HFC-134a), $CF_3$—$CH_2F$, b.p. $-26.5°$ C.
e. Difluoromethane (R-32, HFC-32), $CH_2F_2$, b.p. $-51.6°$ C.
f. Pentafluoroethane (R-125, HFC-125), $CF_3$—$CHF_2$, b.p. $-48.5°$ C.
g. Chlorofluoromethane (R-31, Freon-31), $CH_2ClF$, b.p. $-9.1°$ C.
h. Isobutylene (2-Methylpropene), $(CH_3)_2C{=}CH_2$, b.p. $-6.9°$ C.
i. Propane, $CH_3$—$CH_2$—$CH_3$, b.p. $-42.1°$ C.
j. Butane, $CH_3$—$CH_2$—$CH_2$—$CH_3$, b.p. $-0.5°$ C.
k. Cyclopropane, b.p. $-33°$ C.
l. pentane, $CH_3$—$CH_2$—$CH_2$—$CH_2$—$CH_3$, b.p. $36.1°$ C.
m. isopentane, $(CH_3)_2$—$CH$—$CH_2$—$CH_3$, b.p. $28°$ C.
n. Neopentane (dimethyl propane), $(CH_3)_4$—$C$, b.p. $10°$ C.
o. Propene (propylene), $CH_3$—$CH{=}CH_2$, b.p. $-47.8°$ C.
p. 1-Butene (1-butylene), $CH_3$—$CH_2$—$CH{=}CH_2$, b.p. $-6.3°$ C.
q. cis-2-Butene, $CH_3$—$CH{=}CH$—$CH_3$, b.p. $3.7°$ C.
r. trans-2-Butene, $CH_3$—$CH{=}CH$—$CH_3$, b.p. $1°$ C.
s. Isobutane (2-Methylpropane), $(CH_3)_3CH$, b.p. $-12°$ C.,
t. Dimethyl ether (Methyl ether), $CH_3$—$O$—$CH_3$, b.p. $-24.8°$ C.
u. Supercritical carbon dioxide In a preferred aspect of the invention the Δ9-THC has a purity of at least 95%, preferably, at least 98%, more preferably, at least 99% and most preferably, at least 99.5%.

In a more preferred aspect of the invention the Δ9-THC comprises less than 0.5% of cannabinol, more preferably, less than 0.3% and most preferably, less than 0.2%.

The invention additionally provides a solution of Δ9-THC as described herein.

Accordingly, the invention provides a solution of Δ9-THC in a in a solvent which exists as a gas at room temperature and atmospheric pressure. The solvent can be any solvent described herein for use in the processes of the invention. Thus, the solvent can be an organic solvent having a boiling point below room temperature. Alternatively, the solvent can be an inorganic compound which exists as a gas at room temperature and atmospheric pressure, but which can be maintained as a liquid under conditions of altered temperature and/or pressure conveniently obtainable in laboratory or commercial preparative environments, such as supercritical carbon dioxide.

The solution may comprise, as a solvent, a single compound or a mixture of compounds, each compound being a low boiling point solvent e.g. as described herein. Preferably the solvent will possess one or more of the following properties: low toxicity; low environmental impact; and prior approval for pharmaceutical use. For example, in some embodiments a hydrofluoroalkane (HFA) solvent is used. HFAs are widely used in inhalers and have been recognised as having no toxicity issues.

In embodiments of the invention in which the solution comprises an organic solvent, the solvent will typically have a boiling point below about $20°$ C., preferably below about $0°$ C. The solvent conveniently has a boiling point of from about $-60°$ C. to about $20°$ C., preferably from about $-60°$ C. to about $0°$ C. Preferred boiling point ranges include about $-60$ to about $-40°$ C., about $-40$ to about $-20°$ C. and about $-20$ to about $0°$ C.

The organic solvent of the invention may be any suitable low boiling point solvent, or a mixture of such solvents, having one or more of the properties described herein. In some embodiments, the solvent is a hydrocarbon solvent but other, non-hydrocarbon, organic solvents may also be used, for example low boiling point ethers.

In embodiments in which the solution comprises a hydrocarbon solvent, the hydrocarbon solvent typically comprises one or more ($C_1$-$C_5$) hydrocarbons, optionally substituted by halogen (e.g. a hydrofluoroalkane). The hydrocarbon can be saturated or unsaturated and, if unsaturated, typically comprises one or two unsaturated bonds. In preferred embodiments, the solution comprises one or more ($C_1$-$C_4$) hydrocarbons, one or more ($C_3$-$C_5$) hydrocarbons, and/or one or more ($C_1$-$C_2$) hydrocarbons substituted by one or more halogens, preferably fluoro or chloro.

In a preferred embodiment, the solution comprises one or more propanes, butanes or butenes.

More preferably, the solution comprises one or more of n-propane, isopropane, cyclopropane, n-butane, isobutane and isobutylene.

Most preferably, the solution comprises n-propane, n-butane, isobutane or isobutylene.

In a preferred aspect of the invention the Δ9-THC has a purity of at least 95%, preferably, at least 98%, more preferably, at least 99% and most preferably, at least 99.5% in the solution.

In a more preferred aspect of the invention the Δ9-THC comprises less than 0.5% of cannabinol, more preferably, less than 0.3% and most preferably, less than 0.2% in the solution.

Typically, the Δ9-THC that is extracted from the plant material or produced from the acid by decarboxylation is further purified by recrystallisation and/or column chromatography, with the solvents used in these processes being removed by rotary evaporation or vacuum distillation in a suitable vessel. Δ9-THC as used in the present invention may be prepared or isolated by known techniques, such as described in WO 03/064407.

A solution of Δ9-THC is then made by adding the appropriate solvent, with stirring, to the vessel, which has been cooled to a temperature below the boiling point of the solvent. Once all of the Δ9-THC has dissolved, the solution is then easily transferred to suitable storage containers. Due to the sensitivity to light of the Δ9-THC, the storage containers are typically dark bottles.

The solvent is then allowed to evaporate from the container leaving behind the Δ9-THC. The rate of evaporation can be controlled by variation of the temperature. Evaporation is assisted and decomposition by oxidation of the Δ9-THC is prevented by running a stream of an inert gas, preferably argon, into the container. Preferably, the container is warmed up to at least the boiling point of the solvent. In some embodiments, this may be conveniently achieved passively, by placing the container in an environment maintained at a certain temperature, e.g. about $4°$ C. or room temperature.

Accordingly, the invention provides a process, which comprises preparing a solution of Δ9-THC in a first container, transferring the solution to a second container and evaporating the solvent to leave Δ9-THC.

The present invention has the advantage that the solution is prepared below room temperature, and typically below $0°$ C. In some instances the solution is prepared at a temperature of $-40°$ C. and even $-78°$ C. At these temperatures, the Δ9-THC is very stable and no significant degradation occurs.

The solutions are also easy to handle at these temperatures, which can be reached without difficulty even on the large scales used in manufacturing. Handling of the solutions is also relatively straightforward, being easy to transfer between vessels by pouring or via pipes.

Once the solution has been transferred, the solvent is readily evaporated, whilst keeping the temperature at a low level, because of the low boiling point of the hydrocarbon solvents of the invention. Again, this aids in the prevention of degradation that occurs at the higher temperatures at which Δ9-THC is usually handled.

Residual solvent levels can also be readily minimised, because of their low boiling points. Advantageously, use of low boiling solvents having a boiling point below about 0° C. results in particularly low residual solvent levels.

The applicant has surprisingly found that the processes of the invention provide a Δ9-THC product having improved physical properties. In particular, the evaporation of a low boiling point solvent from a Δ9-THC solution of the invention results in a product having some properties of a crystalline material, rather than the usual glassy structure.

Accordingly, in a further aspect the invention provides a solid Δ9-THC preparation comprising crystalline material. Conveniently, the solid Δ9-THC preparation is obtainable, or is obtained, using the processes of the invention. For example, the Δ9-THC preparation can be obtained by evaporating the solvent from a solution of the invention.

The crystalline material may be present as small regions within a larger glassy structure or may comprise a significant proportion of the Δ9-THC. Preferably, the Δ9-THC comprises more than about 10%, about 20%, about 30%, about 40%, about 50%, about 60% or about 70% crystalline material. More preferably, the Δ9-THC comprises more than about 80% and, most preferably, more than about 90% crystalline material.

The presence of crystalline material has been demonstrated by the presence of peaks of significantly improved sharpness in the solid state spectrum of Δ9-THC obtained using the processes of the invention compared to Δ9-THC obtained using conventional methods. Other methods can be used to confirm the presence of crystalline Δ9-THC, such as X-ray diffraction or polarised microscopy.

The presence of crystalline material results in a Δ9-THC product that is less sticky and easier to handle, especially at low temperatures, e.g. below 0° C. or below room temperature. This significantly simplifies the process of weighing Δ9-THC and transferring to appropriate storage containers.

The presence of crystalline Δ9-THC also opens up the possibility of providing Δ9-THC in powdered from, again providing increased convenience of handling, especially at the low temperatures described herein.

Accordingly, in a preferred embodiment, the solid Δ9-THC preparation comprises Δ9-THC powder. The powder can be provided by abrading, crushing or otherwise physically interacting with a piece of a solid Δ9-THC preparation of the invention. Alternatively, the powder can be provided by spray-drying. Thus, in a further aspect, the invention provides a method of preparing a Δ9-THC preparation comprising preparing a Δ9-THC solution of the invention and spray-drying the solution, thereby producing a Δ9-THC powder.

EXAMPLE 1

A reaction vessel containing Δ9-THC (100 g) is cooled to −20° C. and isobutylene (1 L) is added with stirring. Once the Δ9-THC has dissolved the solution is transferred slowly to a storage vessel, which is kept at around room temperature. A stream of argon gas is passed into the container to aid evaporation of the solvent. Once transfer is complete, gas is continually streamed into the container until all of the solvent has evaporated. The container is then capped and stored in a refrigerator and protected from light.

EXAMPLE 2

A vessel containing Δ9-THC (10 g) is cooled to −20° C. and isobutylene (100 ml) is added with stirring. Once the Δ9-THC has dissolved, the solution is transferred dropwise to 10 sample vessels. A stream of argon gas is passed slowly into the vessels until the solvent has completely evaporated. The containers are then capped and stored refrigerated and protected from light.

EXAMPLE 3

$^{13}$C nuclear magnetic resonance (SS13CNMR) spectroscopy was carried out on Δ9-THC prepared using standard production methods and Δ9-THC obtained by evaporation of solvent from a solution of Δ9-THC in n-propane. Both samples were frozen at −20° C. and analysed by SS13CNMR.

The spectra observed were similar for both samples. However, the peaks in the spectrum of the sample isolated from a solution in n-propane were significantly sharper, indicating the presence of crystalline material. The sample obtained using standard methods was largely amorphous in structure.

Thus, the data showed that Δ9-THC obtained from the evaporation of a solution of Δ9-THC in n-propane contained crystalline material.

The invention hence provides methods and compositions for handling Δ9-THC.

What is claimed is:

1. A process, comprising combining Δ9-THC with a solvent at a temperature of 0° C. or below in a first container so as to prepare a solution of the Δ9-THC in the solvent, transferring the solution to a second container and evaporating the solvent to leave Δ9-THC, wherein the solvent exists as a gas at room temperature and atmospheric pressure and wherein the solvent is an organic solvent.

2. The process of claim 1 wherein the solvent is an organic solvent having a boiling point below about 20° C.

3. The process of claim 2, wherein the solvent has a boiling point below about 0° C.

4. The process of claim 2 wherein the solvent comprises one or more ($C_1$-$C_4$) hydrocarbons, optionally substituted by one or more halogens.

5. A process, comprising combining Δ9-THC with a solvent at a temperature of 0° C. or below in a first container so as to prepare a solution of the Δ9-THC in the solvent, transferring the solution to a second container and evaporating the solvent to leave Δ9-THC, wherein the solvent exists as a gas at room temperature and atmospheric pressure and wherein the solvent is an organic solvent, wherein the solvent comprises one or more propanes, butanes or butenes.

6. The process of claim 5 wherein the solvent comprises one or more of n-propane, isopropane, cyclopropane, n-butane, isobutane and isobutylene.

7. The process of claim 6 wherein the solvent comprises n-propane, n-butane, isobutane or isobutylene.

8. The process of claim 1 wherein the Δ9-THC has a purity of at least 95%.

9. The process of claim 1 wherein the Δ9-THC comprises less than 0.5% of cannabinol.

10. A solution of Δ9-THC in an organic solvent at a temperature of 0° C. or below and wherein the solvent exists as a gas at room temperature and atmospheric pressure and the solvent comprises one or more propanes, butanes or butenes.

11. The solution of claim 10 wherein the solvent is an organic solvent having a boiling point below about 20° C.

12. The solution of claim 11, wherein the solvent has a boiling point below about 0° C.

13. The solution of claim 10 wherein the solvent comprises one or more of n-propane, isopropane, cyclopropane, n-butane, isobutane and isobutylene.

14. The solution of claim 13 wherein the hydrocarbon solvent comprises n-propane, n-butane, isobutane or isobutylene.

15. The solution of claim 10 wherein the Δ9-THC has a purity of at least 95%.

16. The solution of claim 10 wherein the Δ9-THC comprises less than 0.5% of cannabinol.

17. A method of preparing a Δ9-THC preparation comprising preparing the solution of claim 10 and spray-drying the solution, thereby producing a Δ9-THC powder.

* * * * *